United States Patent [19]

Lamberti et al.

[11] 4,152,515
[45] May 1, 1979

[54] BUILDERS FOR DETERGENT COMPOSITIONS

[75] Inventors: Vincent Lamberti, Upper Saddle River; Mark D. Konort, Haworth, both of N.J.

[73] Assignee: Lever Brothers Company, New York, N.Y.

[21] Appl. No.: 787,193

[22] Filed: Apr. 13, 1977

Related U.S. Application Data

[60] Division of Ser. No. 678,094, Apr. 19, 1976, abandoned, which is a continuation of Ser. No. 348,567, Apr. 6, 1973, abandoned, which is a continuation of Ser. No. 92,170, Nov. 23, 1970, abandoned.

[51] Int. Cl.$^2$ .............. C07C 59/23; C07C 149/20; C07D 295/18; C07D 295/22
[52] U.S. Cl. .............. 544/107; 252/89 R; 252/135; 252/524; 252/526; 252/527; 252/530; 252/533; 252/536; 252/539; 252/542; 252/545; 252/546; 252/552; 252/554; 252/558; 260/501.1; 260/501.15; 260/501.17; 260/501.19; 260/501.21; 544/110; 562/581; 562/583; 562/594
[58] Field of Search ............ 260/537 S, 535 P, 501.1, 260/501.15, 501.17, 501.19, 501.21; 544/107, 110; 562/581, 583

[56] References Cited

U.S. PATENT DOCUMENTS

| | | | |
|---|---|---|---|
| 2,581,514 | 1/1952 | Chilcote | 260/537 S |
| 3,446,807 | 5/1969 | Wagner | 260/537 S |
| 3,772,382 | 11/1973 | Dannals | 260/537 S |

OTHER PUBLICATIONS

Chem. Abstracts, 58: 12451i–12452b (1963).
Chem. Abstracts, 42: 4134h–4135d.

*Primary Examiner*—Vivian Garner
*Attorney, Agent, or Firm*—Michael J. Kelly; James J. Farrell; Melvin H. Kurtz

[57] ABSTRACT

There are disclosed herein novel builder salts of alkyloxysuccinic acids, alkyloxyhydroxysuccinic acids, alkylthiosuccinic acids, alkylthiohydroxysuccinic acids, and the sulfoxide and sulfone derivatives of the alkylthiosuccinic and alkylthiohydroxysuccinic acids. The new builder compounds can be generally represented as follows:

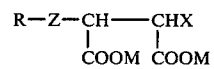

wherein Z is selected from the group consisting of O, S, SO and SO$_2$; X is H or OH; R is an alkyl radical containing from 6 to 30 carbon atoms and M is selected from the group consisting of alkali metal cations, ammonium and substituted ammonium. These new builder compounds can be substituted in detergent compositions for existing builders containing phosphorous or nitrogen without impairing and in some cases improving the efficiency of such detergent compositions.

1 Claim, No Drawings

BUILDERS FOR DETERGENT COMPOSITIONS

This application is a Divisional of Ser. No. 678,094 filed Apr. 19, 1976, now abandoned; which in turn was a continuation of Ser. No. 348,567 filed Apr. 6, 1973, now abandoned; which in turn was a continuation of Ser. No. 92,170 filed Nov. 23, 1970, now abandoned.

BACKGROUND OF THE INVENTION

Field of the Invention

The present invention relates to new builder salts of alkyloxysuccinic acids, alkyloxyhydroxysuccinic acids, alkylthiosuccinic acids, alkylthiohydroxysuccinic acids, and the sulfoxide and sulfone derivatives of the alkylthiosuccinic and alkylthiohydroxysuccinic acids which do not contain phosphorus or nitrogen and more specifically to detergent compositions containing these new builder compositions which are biodegradable and have similar detergent-building properties as existing builders.

The builder salt compounds of the alkyloxysuccinic acids, alkyloxyhydroxysuccinic acids, alkylthiosuccinic acids, alkylthiohydroxysuccinic acids, and the sulfoxide and sulfone derivatives of the alkylthiosuccinic and alkylthiohydroxysuccinic acids of the present invention can be generally represented as follows:

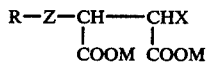

wherein Z is selected from the group consisting of O, S, SO and $SO_2$; X is H or OH; R is an alkyl radical having 6 to 30 carbon atoms and M is selected from the group consisting of alkali metal, ammonium, and substituted ammonium cations.

These compounds have one or more asymmetric carbon atoms and therefore can exist in optically active forms as well as optically inactive mixtures (racemates). For purposes of this invention the compounds as defined are intended to include all of the stereoisomeric forms and mixtures thereof, e.g., d, l and dl for one asymmetric carbon and d, d', l, l', dl and d'l' for two dissimilar asymmetric carbons. A complete discussion of stereoisomeric forms will be found in Fieser and Fieser, "Organic Chemistry", Reinhold Publishing Co., 1956, Chapter 11, pages 249–294 which is incorporated herein as a reference.

HISTORICAL BACKGROUND OF THE INVENTION AND DESCRIPTION OF THE PRIOR ART

In recent years, studies have been conducted concerning the problem of eutrophication. Eutrophication can be defined as a natural process of enrichment of waters with nutrients, such as phosphorus and nitrogen compounds, at a slow rate. Eutrophication can be detrimental, since it may cause increased algal growth and algal scums which are unaesthetic, odorous, distasteful and clog filters of treatment plants. It has been postulated that various human activities have accelerated the process. Contributing factors in the eutrophication of lakes, streams and estuaries are natural runoff, agricultural drainage, ground water, precipitation, sewage and waste effluents.

It has been postulated that the phosphorus-containing builders present in detergent compositions can be a factor in eutrophication, and therefore any substitutes which do not contain phosphorus may decrease to some extent the eutrophication problem. Thus, those skilled in the art have expended a great deal of time and money to find suitable materials to reduce or replace the existing phosphate builders in detergent compositions.

The builder compounds of the present invention behave as precipitant builders unlike the tripolyphosphate builders not found in detergent compositions which act primarily as sequestrant builders. While many precipitant builders are now known to the art, these builders have many disadvantages. For example, the oxalates are toxic, the carbonates will not precipitate all of the calcium within the necessary time requirements and soap, which bears the closest analogy to the compounds of the present invention, requires twice the number of moles of the present compounds to precipitate an equivalent amount of calcium ions. In addition, soap will leave an unsightly scum which will deposit on the clothes making it unsuitable as a builder in detergent compositions.

As explained above, the builder compounds of the present invention are the salts of acids having the following general formula:

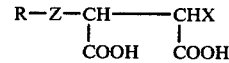

wherein Z is selected from the group consisting of O, S, SO and $SO_2$; X is H or OH and R is an alkyl radical having 6 to 30 carbon atoms.

Compounds where X is H and Z is O or S have been suggested in the prior art as detergents, emulsifying agents or wetting agents. More specifically, the alkylthiosuccinate is described in U.S. Pat. No. 2,581,514, issued to W. B. Chilcote and the alkyloxysuccinate is described in U.S. Pat. No. 2,377,246, issued to L. P. Kyrides. While these compounds have been suggested as detergents, there was never any indication that they would make excellent precipitant builders and, therefore, could be used in place of the existing phosphate or nitrogen builders. It was totally unexpected to find that wetting agents or emulsifiers could act as builders in detergent systems. The compounds where X is OH and Z is O and S and where X is OH and H and Z is SO and $SO_2$ are novel materials which have not been described or suggested in the art.

SUMMARY OF THE INVENTION

It is therefore an object of the present invention to provide novel builder compounds which are free of phosphorus and with the proper cations free of nitrogen, but which are as efficient as existing builders containing phosphorus and nitrogen.

Another object of the present invention is to provide detergent compositions containing the novel builder compounds.

Still another object of the invention is to provide new builder compounds which can be synthesized at low cost and which are also biodegradable.

It has now been discovered that effective detergent builder compounds can be produced from the salts of alkyloxysuccinic acids, alkyloxyhydroxysuccinic acids, alkylthiosuccinic acids, alkylthiohydroxysuccinic acids, and the sulfoxide and sulfone derivatives of the alkylthiosuccinic and alkylthiohydroxysuccinic acids. Some of these new builder compounds, which as explained above, will act as precipitant builders as opposed to sequestrant builders when higher chain lengths are used say above $C_8$, but do not have the disadvantage of existing precipitant builders such as soap. More specifically, while these new builder compounds of the present invention will form a precipitate with the calcium ions present in the water, the precipitate formed is very finely divided and does not form a heavy scum material on the clothes or in the water. Further, the precipitate can provide an unexpected advantage inasmuch as when it is deposited on the clothes during the washing process, the clothes have a feel similar to that of clothes treated with a fabric softener.

The new builder compounds of the present invention are prepared by ordinary addition reactions. Thus, the alkyloxysuccinates and alklyoxyhydroxysuccinates are prepared by the reaction of alkanols and maleic esters or epoxy succinic esters, respectively in the presence of a suitable catalyst followed by saponification. The alkylthiosuccinates and alkylthiohydroxysuccinates are prepared by the reaction of alkylmercaptans and maleic anhydride or epoxysuccinic esters, respectively in the presence of a suitable catalyst followed by saponification. Alternatively, mercaptosuccinic acid may be reacted with alpha-olefins in the presence of a free radical catalyst to produce the alkylthiosuccinic acid followed by neutralization with the appropriate alkaline material. The sulfoxides and sulfones are prepared by reacting the appropriate thio compound with hydrogen peroxide according to the methods described on pages 471-472 in the text "Reagents for Organic Synthesis" by Fieser and Fieser, published by John Wiley and Sons Inc., 1967 and which is incorporated as reference herein.

The aforesaid reactions produce compounds having the following structure:

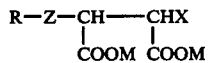

70 wherein Z is O or S, X is H or OH, R is an alkyl group having a chain length from 6 to 30 carbon atoms and M is selected from the group consisting of alkali metal cations, ammonium cations, and substituted ammonium cations such as alkanolammonium, morpholinium, alkylammonium, mono-, di- and trialkanolammonium and tetramethyl ammonium. While the alkyl chain can be anywhere from $C_6$ to $C_{30}$, the preferred chain length is from $C_{10}$ to $C_{22}$. It appears that chain lengths below $C_{10}$ are not as efficient as builders than chain lengths above $C_{10}$. Also the unrefined lower alkylthiosuccinates may have an odor which could be objectionable to the consumer. Chain lengths above $C_{22}$ are not commercially available at the present time and, therefore, would materially increase the cost of the builder compounds and also may cause solubility problems.

Applicants have also found that the oxygen atom, sulfur atom, sulfoxide or sulfone radicals can be linked to a primary, secondary or tertiary carbon atom without materially affecting the building properties of the final compounds of the invention. However, compounds in which the oxygen or sulfur atoms or sulfoxide or sulfone radicals are linked to a tertiary carbon appear to be less biodegradable than compounds in which the atoms or radicals are linked to a primary or secondary carbon atom.

According to this invention, excellent cleaning results can be obtained by using the succinate builders described above with a wide range of detergent surface active materials. The succinate builders can be used singularly, in combination with each other or with other builders such as sodium nitrilotriacetate, sodium ethylenediaminetetracetate, sodium tripolyphosphate, sodium and potassium pyrophosphate and carboxyl derivatives of polysaccharides. It has been found that when the builders of the present invention are used with other builders, such as those stated above, the detergent building properties are enhanced.

In the detergent compositions of the present invention the only essential ingredients are the detergent surface active material and the succinate builder. The weight percent of the builder present in the detergent compositions is from about 1% to about 95% and preferably from about 20% to about 60%. If the succinate compounds are used as softening agents, amounts from about 1% to about 10% by weight may be used.

The detergent surface active compounds which can be used in the compositions of this invention include anionic, nonionic, zwitterionic, ampholytic detergent compounds and mixtures thereof. These suitable substances are outlined at length below.

(a) Anionic detergent compositions which can be used in the compositions of this invention include both soap and non-soap detergent compounds. Examples of suitable soaps are the sodium, potassium, ammonium and alkylolammonium salts of higher fatty acids ($C_{10}$-$C_{20}$). Particularly useful are the sodium or potassium salts of the mixtures of fatty acids derived from coconut oil and tallow, i.e., sodium or potassium tallow and coconut soap and tall oil. Examples of anionic organic non-soap detergent compounds are the water soluble salts, e.g. alkali metal salts of organic sulfuric reaction products having in their molecular structure an alkyl radical containing from about 8 to about 22 carbon atoms and a radical selected from the group consisting of sulfonic acid and sulfuric acid ester radicals. (Included in the term alkyl is the alkyl portion of higher acyl radicals.) Important examples of the synthetic detergents which form a part of the compositions of the present invention are the sodium or potassium alkyl sulfates especially those obtained by sulfating the higher alcohols ($C_8$-$C_{18}$ carbon atoms) produced by reducing the glycerides of tallow or coconut oil; sodium or potassium alkyl benzenesulfonates in which the alkyl group contains from about 9 to about 20 carbon atoms and in which the alkyl group is attached to the benzene ring in either the one position or at the secondary positions such as in LAS*, sodium p-(2-dodecyl)benzenesulfonate, sodium p-(2-octadecyl)benzenesulfonate and sodium p-(3-dodecyl)benzenesulfonate; sodium alkyl glyceryl ether sulfonates, especially those ethers of the higher alcohols derived from tallow and coconut oil and synthetic alcohols derived from petroleum; sodium coconut oil fatty acid monoglyceride sulfates and sulfonates; sodium or potassium salts of sulfuric acid esters of the reaction product of one mole of a higher fatty alcohol (e.g., tallow or coconut oil alcohols) and about 1 to 6 moles of ethylene oxide per molecule and in which the alkyl radicals contain about 9 to about 18 carbon atoms; the reaction products of fatty acids esterified with isethionic acid and neutralized with sodium hydroxide where, for example, the fatty acids are derived from coconut oil; sodium or potassium salts of fatty acid amides of methyl taurine; sodium or potassium alkane sulfonates such as those derived by reacting alpha-olefins containing 8 to 20 carbon atoms with sodium bisulfite and those derived by reacting paraffins with $SO_2$ and Cl₂ and then hydrolyzing with a base to produce a random sulfonate; alpha-olefinsulfonates and hydroxyalkanesulfonates such as those derived by reacting alphaolefins with SO₃ and then hydrolizing/neutralizing the reaction product; and others known in the art.

Sodium linear secondary alkyl (C₁₀–C₁₅) benzenesulfonate.

(b) Nonionic synthetic detergents may be broadly defined as compounds which do not ionize in water solution. For example, a well-known class of nonionic synthetic detergents is made available on the market under the trade name of "Pluronic". These compounds are formed by condensing ethylene oxide with a hydrophobic base formed by the condensation of propylene oxide with propylene glycol. The hydrophobic portion of the molecule which, of course, exhibits water insolubility has a molecular weight of from about 1,500 to 1,800. The addition of polyoxyethylene radicals to this hydrophobic portion tends to increase the water solubility of the molecule as a whole and the liquid character of the product is retained up to the point where polyoxyethylene content is about 50% of the total weight of the condensation product.

Other suitable nonionic synthetic detergents include:

(1) The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amount equal to 5 to 25 moles of ethylene oxide per mole of alkyl phenols. The alkyl substituent in such compounds may be derived from polymerized propylene, di-isobutylene, octene, nonene and dodecene, for example.

(2) Those derived from the condensation of ethylene oxide with the product resulting from the reaction of propylene oxide and ethylenediamine. For example, compounds containing from about 40% to about 80% polyoxyethylene by weight and having a molecular weight of from about 5,000 to about 11,000 resulting from the reaction of ethylene oxide with a hydrophobic base constituted of the reaction product of ethylenediamine and excess propylene oxide, said hydrophobic base constituted of the reaction product of ethylenediamine and excess propylene oxide, said hydrophobic base having a molecular weight of the order of 2,500 to 3,000 are satisfactory.

(3) The condensation product of aliphatic alcohols having from 8 to 18 carbon atoms, in either straight chain or branched chain configuration, with ethylene oxide, e.g., Neodol 45-11*, and a coconut alcohol-ethylene oxide condensate having from 6 to 30 moles of ethylene oxide per mole of coconut alcohol, the coconut alcohol fraction having from 10 to 14 carbon atoms.

A synthetic C₁₄–C₁₅ linear primary alcohol - 11 mole ethylene oxide adduct.

(4) Long chain tertiary amine oxides corresponding to the following general formula, $R_1R_2R_3N \rightarrow O$, wherein $R_1$ is an alkyl radical of from about 8 to 18 carbon atoms and $R_2$ and $R_3$ are each methyl, ethyl or hydroxyethyl radicals. The arrow in the formula is a conventional representation of a semi-polar bond. Examples of amine oxides suitable for use in this invention include dimethyldecylamine oxide, dimethyldodecylamine oxide, dimethyltetradecylamine oxide, dimethylhexadecylamine oxide, dimethyloctadecylamine oxide, and N,N-bis(hydroxyethyl)dodecylamine oxide.

(5) Long chain tertiary phosphine oxides corresponding to the following formula $RR'R''P \rightarrow O$, wherein R is an alkyl, alkenyl or monohydroxyalkyl radical ranging from 10 to 18 carbon atoms in chain length and R' and R" are each alkyl or monohydroxyalkyl groups containing from 1 to 3 carbon atoms. The arrow in the formula is a conventional representation of a semi-polar bond. Examples of suitable phosphine oxides are:

dimethyldodecylphosphine oxide,
dimethyltetradecylphosphine oxide,
ethylmethyltetradecylphosphine oxide,
cetyldimethylphosphine oxide,
dimethylstearylphosphine oxide,
cetylethylpropylphosphine oxide,
diethyldodecylphosphine oxide,
diethyltetradecylphosphine oxide,
bis(hydroxymethyl)dodecylphosphine oxide,
bis(2-hydroxyethyl)dodecylphosphine oxide,
2-hydroxypropylmethyltetradecylphosphine oxide,
dimethyloleylphosphine oxide, and
dimethyl-2-hydroxydodecylphosphine oxide.

(6) Dialkyl sulfoxides corresponding to the following formula, $RR'S \rightarrow O$, wherein R is an alkyl, alkenyl, beta- or gamma-monohydroxyalkyl radical or an alkyl or beta- or gamma-monohydroxyalkyl radical containing one or two other oxygen atoms in the chain, the R groups ranging from 10 to 18 carbon atoms in chain length, and wherein R' is methyl, ethyl or alkylol. Examples of suitable sulfoxide compounds are:

dodecyl methyl sulfoxide
tetradecyl methyl sulfoxide
3-hydroxytridecyl methyl sulfoxide
2-hydroxydodecyl methyl sulfoxide
3-hydroxy-4-decyloxybutyl methyl sulfoxide
3-hydroxy-4-dodecyloxybutyl methyl sulfoxide
2-3-decyloxypropyl methyl sulfoxide
2-hydroxy-3-dodecyloxypropyl methyl sulfoxide
dodecyl ethyl sulfoxide
2-hydroxydodecyl ethyl sulfoxide
dodecyl 2-hydroxyethyl sulfoxide (c) Ampholytic synthetic detergents can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group. Examples of compounds falling within this definition are sodium 3-dodecylaminopropionate, sodium 3-dodecylaminopropanesulfonate and sodium N-(2-hydroxydodecyl)-N-methyl-taurate.

(d) Zwitterionic synthetic detergents can be broadly described as derivatives of aliphatic quaternary ammonium compounds, sulfonium compounds and phosphonium compounds in which the aliphatic radical may be straight chain or branched and wherein one of the aliphatic substituents contains from about 8 to 18 carbon atoms and one contains an anionic water solubilizing group. Examples of compounds falling within this definition are 3-(N,N-dimethyl-N-hexadecylammonio)propane-1-sulfonate, 3-(N,N-dimethyl-N-hexadecylammonio)-2-hydroxypropane-1-sulfonate, 3-(dodecylmethylsulfonium) propanesulfonate, and 3-(cetylmethylphosphonium)ethanesulfonate.

In addition to the essential ingredients in the detergent composition, other optional ingredients may also be added. Examples of the optional ingredients are perfumes, colorants, fabric softening agents, fungicides, germicides, enzymes, fluorescent dyes, antiredeposition agents, hydrotropes and in the case of liquid compositions, opacifiers and organic solvents. Other ingredients such as bleaches, i.e., sodium perborate with or without activators and chlorine releasing compounds and inorganic salts such as sodium carbonate, sodium sulfate, sodium chloride and sodium silicate may also be present.

The following examples will illustrate further the present invention without, however, limiting the same thereto. All percentages in the examples are by weight.

The detergent formulations set forth in the examples are prepared by blending together the recited components and are then tested for detergency or cleansing ability in the Terg-O-Tometer Test wherein the washing conditions are as follows (unless otherwise indicated): 65% Dacron-35% cotton VCD (vacuum cleaner dust) cloth; 120° F.; 180 ppm water (2:1 $Ca^{++}/Mg^{++}$); 0.2% concentration of the total formulation in the washing solution; pH 10.0. (The pH of the washing solutions given herein was adjusted, where necessary, by the addition of caustic (NaOH) or sulfuric acid thereto).

The average detergency units (DU) of the formulations is the final reflectance of the washed cloth minus the initial reflectance of the soiled cloth (the average of two runs), the reflectance being measured with a Gardner Automatic Color Difference Meter, Model AC-3.

The following abbreviations have been used in the tables and examples: Neodol 45-11 is a nonionic surfactant which is an adduct of a modified Oxo type $C_{14}$-$C_{15}$ alcohol with an average of 11 moles of ethylene oxide; $C_{14}$-$C_{16}$ HAMT is an ampholytic surfactant which is sodium hydroxyalkyl ($C_{14}$-$C_{16}$) N-methyltaurate; sulfobetaine DCH is a zwitterionic surfactant which is cocodimethylsulfopropyl betaine; $C_{15}$-$C_{18}$ AOS is sodium $C_{15}$-$C_{18}$ α-olefin sulfonate; DU is detergency units; and bal is balance.

PREPARATION OF DISODIUM n-ALKYLTHIOSUCCINATE

Examples 1 and 2

I. Disodium n-tetradecylthiosuccinate 12.2 g n-tetradecylthiosuccinic anhydride prepared according to the method of Zienty et al. [J. Org. Chem. 27, 3144 (1962)] was dissolved in methanol. Then, 3.6 g of sodium hydroxide in 15 ml of water was added and the mixture stirred for one hour. The crystalline precipitate was filtered off, dissolved in 150 ml of hot water and decolorized with charcoal. The filtrate from the charcoal treatment was then concentrated in vacuo and poured into acetone to precipitate the disodium n-tetradecylthiosuccinate. After drying the product in a vacuum oven, the yield was 13.2 g (0.24% moisture). The structure of the product was confirmed by NMR analysis.

II. Disodium n-dodecylthiosuccinate

This material was prepared as in Example 1, except that n-dodecylthiosuccinic anhydride, prepared according to the Zienty et al. method (supra) was used.

DISODIUM α-OCTADECYLOXY-β-HYDROXYSUCCINATE

Example 3

Epoxysuccinic acid was first prepared using the method of Payne and Williams, J. Org. Chem. 24 55 (1959). The epoxysuccinic acid was then converted into the Ag salt and reacted with methyl iodide to form dimethyl epoxysuccinate using the procedure described by Schork et al., Ann. 348 302 (1906), for the preparation of dimethyl epoxyfumarate.

Distilled dimethyl epoxysuccinate, 20.0 g (0.125 mole), was added dropwise to a stirred mixture of octadecyl alcohol, 67.5 g (0.25 mole), and $SnCl_4$ catalyst, 2 g, at 85° C. After the addition was complete (30 min.), the temperature was raised and maintained at 115° C. for three hours. After cooling, an aqueous solution of $Na_2CO_3$ was added to neutralize the catalyst. The resulting precipitate was filtered off and washed with ether. Evaporation of the ether filtrate gave a residue (59 g) of crude diester product.

The diester product was saponified with 300 ml of methanol containing 0.27 mole of sodium hydroxide by refluxing the mixture for 2½ hours. The precipitated disodium salt was filtered, digested with ethyl ether and refiltered. The product was then recrystallized from water-ethanol. The dried crystalline disodium salt, 25 g (45% yield), was identified by infrared and NMR analyses. Purity (by titration with perchloric acid): 93%.

DETERGENT BUILDING PROPERTIES OF n-ALKYLTHIOSUCCINATES

Examples 4-9

| Washing Conditions: | Terg-O-Tometer; Dacron/Cotton VCD Cloth; 120° F.; 180 ppm water (2:1 $Ca^{++}/Mg^{++}$); 0.2% concentration of total formulation; pH = 10.0 | | | | | |
|---|---|---|---|---|---|---|
| Component | 4 | 5 | 6 | 7 | 8 | 9 |
| 1. Disodium n-dodecyl-thiosuccinate | 50 | — | — | 25 | — | — |
| 2. Disodium n-tetra-decylthiosuccinate | — | 50 | — | — | 25 | — |
| 3. Sodium tripoly-phosphate | — | — | 50 | — | — | 25 |
| 4. Sodium linear secondary alkyl ($C_{10}$-$C_{15}$) benzene sulfonate | 18 | 18 | 18 | 9 | 9 | 9 |
| 5. Sodium silicate solids (2.4 $SiO_2$/$Na_2O$) | 10 | 10 | 10 | 5 | 5 | 5 |
| 6. Water | bal | bal | bal | bal | bal | bal |
| Average Detergency Units (DU) : | 26.6 | 26.8 | 27.5 | 22.5 | 20.7 | 23.2 |
| % Detergency efficiency vs. corresponding controls (i.e., 4 vs 6, 5 vs 6, 7.vs 9, 8 vs 9) : | 97 | 98 | | 97 | 90 | |

DETERGENT BUILDING PROPERTIES OF n-ALKYLTHIOSUCCINATES

Examples 10-17

| Washing Conditions: | Terg-O-Tometer; Dacron/Cotton VCD Cloth; 120° F.; 180 ppm water (2:1 $Ca^{++}1Mg^{++}$); 0.2% concentration of total formulation; pH = 10.0 | | | | | | | |
|---|---|---|---|---|---|---|---|---|
| Component | 10 | 11 | 12 | 13 | 14 | 15 | 16 | 17 |
| 1. Disodium n-tetra- | 50 | — | 50 | — | 50 | — | 50 | — |

-continued

| Washing Conditions: | Terg-O-Tometer; Dacron/Cotton VCD Cloth; 120° F.; 180 ppm water (2:1 $Ca^{++}/Mg^{++}$); 0.2% concentration of total formulation; pH = 10.0 | | | | | | | |
|---|---|---|---|---|---|---|---|---|
| Component | 10 | 11 | 12 | 13 | 14 | 15 | 16 | 17 |
| decylthiosuccinate | | | | | | | | |
| 2. Sodium tripoly-phosphate | — | 50 | — | 50 | — | 50 | — | 50 |
| 3. Sodium silicate solids (2.4 $SiO_2$/$Na_2O$) | 10 | 10 | 10 | 10 | 10 | 10 | 10 | 10 |
| 4. Neodol 45-11 | 10 | 10 | — | — | — | — | — | — |
| 5. $C_{14}$-$C_{16}$ HAMT | — | — | 18 | 18 | — | — | — | — |
| 6. Sulfobetaine DCH | — | — | — | — | 18 | 18 | — | — |
| 7. $C_{15}$-$C_{18}$ AOS | — | — | — | — | — | — | 18 | 18 |
| 8. Water | bal | bal | bal | bal | bal | bal | bal | bal |
| Average Detergency Units (DU): | 24.8 | 25.8 | 25.1 | 27.4 | 27.7 | 28.2 | 27.9 | 27.5 |
| % Detergency efficiency vs. corresponding controls (i.e., 10 vs 11, 12 vs 13, 14 vs 15, 16 vs 17): | 96 | | 92 | | 98 | | 102 | |

Examples 18–21

| Washing Conditions: | Terg-O-Tometer; Dacron/Cotton VCD Cloth; 120° F.; 180 ppm water (2:1 $Ca^{++}/Mg^{++}$); 0.2% concentration of total formulation; pH = 10.0 | | | |
|---|---|---|---|---|
| Component | 18 | 19 | 20 | 21 |
| 1. Disodium n-dodecyloxysuccinate | 50 | — | — | — |
| 2. Disodium n-hexadecyloxysuccinate | — | 50 | — | — |
| 3. Disodium α-octadecyloxy-β-hydroxysuccinate | — | — | 50 | — |
| 4. Sodium tripolyphosphate | — | — | — | 50 |
| 5. Sodium silicate solids (2.4 $SiO_2$/$Na_2O$) | 10 | 10 | 10 | 10 |
| 6. Sodium linear secondary alkyl ($C_{10}$-$C_{15}$)benezenesulfonate | 18 | 18 | 18 | 18 |
| 7. Water | bal | bal | bal | bal |
| Average Detergency Units (DU): | 28.1 | 28.8 | 27.3 | 27.6 |
| % Detergency efficiency compared to control formulation: | 102 | 104 | 99 | |

Example 22

Preparation of Disodium n-Dodecylsulfonylsuccinate

Disodium n-dodecylthiosuccinate, 7.0 g (19.3 m moles), prepared according to Example 2 is dissolved in 25 ml of water and heated to 40° C. After adding 0.3 g of 50% aqueous sodium hydroxide, 55.8 ml of 5.15% sodium hypochlorite solution (38.6 m moles) is slowly added, while stirring, over a one hour period at 40° C. After stirring the mixture at 40° C. overnight, the mixture is cooled and the solid product filtered. Yield 4.9 g; infrared spectrum (Nujol Mull) shows the presence of new absorption bands at 7.53 and 8.85µ consistent for the sulfone derivative. Some intermediate sulfoxide product is also present (9.62µ).

Example 23

Preparation of Disodium n-Dodecylsulfinylsuccinate 6.5 g of n-dodecylthiosuccinic acid, which is prepared according to the method of Zienty et al. [J. Org. Chem. 27 3144 (1962)], is dissolved in 50 ml of acetone. Then 2.2 ml of 30% $H_2O_2$ is added dropwise while maintaining the reaction mixture at 15°–20° C. After standing overnight, the reaction mixture is cooled to 0° C. and filtered to remove a small amount of insoluble matter, 0.5 g. The filtrate is evaporated to a small volume and the resulting precipitate filtered and washed with ether to give 3.9 g of crude n-dodecylsulfinylsuccinic acid. Recrystallization from 200 ml of hexane gives a purified product, m.p. 99.2°–101.3° C.; neutralization equivalent by titration with standard sodium hydroxide: found, 164; theoretical, 167.

Three grams of the sulfoxide of n-dodecylthiosuccinic acid prepared above is dissolved in ethanol and mixed with a solution of 1.4 g of sodium ethylate dissolved in 25 ml of ethanol. The precipitated product is then filtered and dried in vacuo to give 3.3 g of disodium n-dodecylsulfinylsuccinate.

Examples 24–27

| Washing Conditions: | Terg-O-Tometer; Dacron/Cotton VCD Cloth; 120° F.; 180 ppm water (2:1 $Ca^{++}/Mg^{++}$); 0.2% concentration of total formulation; pH = 10.0 | | | |
|---|---|---|---|---|
| Component | 24 | 25 | 26 | 27 |
| 1. Disodium n-dodecyl-sulfinylsuccinate | 50 | — | — | — |
| 2. Disodium n-dodecyl-sulfonylsuccinate | — | — | 50 | 13 |
| 3. Sodium tripolyphosphate | — | 50 | — | 50 |
| 4. Sodium silicate solids (2.4 $SiO_2$/$Na_2O$) | 10 | 10 | 10 | 10 |
| 5. Sodium linear secondary alkyl ($C_{10}$-$C_{15}$) benzene sulfonate | 18 | 18 | 18 | 18 |
| 6. Water | bal | bal | bal | bal |
| Average Detergency Units (DU): | 29.1 | 29.0 | 26.5 | 28.2 |
| % Detergency efficiency compared to control formulations (i.e., 24 vs 25 and 26 vs 27) | 100 | | 94 | |

Example 28

Disodium α-n-Dodecylthio-β-Hydroxysuccinate

Sodium methoxide, 1.08 g (0.02 mole), dissolved in 20 ml of methanol, is added to a solution of 12.1 g (0.06 mole) of n-dodecyl mercaptan in 120 ml of dioxane. The mixture is partially distilled to remove the methanol. Dimethyl epoxysuccinate, 10 g (0.06 mole) is then added while stirring the mixture and maintaining the temperature at 85° C. The mixture is refluxed for one hour and evaporated in vacuo to remove the dioxane solvent.

The crude diester residue from above is then dissolved in 70 ml of methanol and brought to reflux. A solution of 4.4 g of sodium hydroxide in 100 ml of methanol is then added and the mixture refluxed for three hours. The resulting precipitate of crude disodium salt is filtered, washed with methanol and dried. The dry salt is then dispersed in water and the pH adjusted to 2 with dilute hydrochloric acid to precipitate the diacid. The diacid is then purified by extracting with methanol followed by filtering, evaporation of the filtrate and recrystallizing the resulting residue from ethanol/water to obtain α-n-dodecylthio-β-hydroxysuccinic acid. The desired disodium salt is then obtained by dissolving the diacid in methanol and mixing with a methanolic solution containing a slight excess over the theoretical amount of sodium methoxide required to neutralize the diacid. The product, which precipitates, is filtered, washed with methanol and dried to give the desired disodium α-n-dodecylthio-β-hydroxysuccinate.

The disodium α-n-dodecyithio-β-hydroxysuccinate when formulated with a surfactant such as sodium linear secondary alkyl ($C_{10}$-$C_{15}$) benzenesulfonate has acceptable building properties.

Example 29

Disodium α-n-Dodecylsulfinyl-β-Hydroxysuccinate

The α-n-dodecylthio-β-hydroxysuccinic acid obtained as an intermediate in Example 28 is converted into the corresponding sulfoxide using the procedure described in Example 23 for converting n-dodecylthiosuccinic acid into disodium n-dodecylsulfinylsuccinate. The material when formulated with linear secondary alkyl ($C_{10}$-$C_{15}$) benzenesulfonate has acceptable building properties.

Example 30

Disodium α-n-Dodecylsulfonyl-β-Hydroxysuccinate

Disodium α-n-dodecylthio-β-hydroxysuccinate, prepared according to Example 28, is converted into the corresponding sulfone using the procedure of Example 22 for converting disodium n-dodecylthiosuccinate into disodium n-dodecylsulfonylsuccinate. Disodium α-n-dodecylsulfonyl-β-hydroxysuccinate when formulated with a surfactant such as linear secondary alkyl ($C_{10}$-$C_{15}$) benzenesulfonate has acceptable building properties.

It is intended to cover all changes and modifications of the preferred embodiments of the invention, herein chosen for the purpose of illustration, which do not constitute departures from the spirit and scope of the invention.

What is claimed is:

1. Compounds having the general formula:

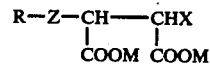

wherein R is an alkyl radical having about 10 to about 22 carbon atoms, M is selected from the group consisting of alkali metal, ammonium, morpholinium, alkylammonium, monoalkanolammonium, dialkanolammonium, trialkanolammonium, and tetra methyl ammonium cations and Z is selected from the group consisting of O, S, SO, and $SO_2$, and X is OH.

* * * * *

UNITED STATES PATENT AND TRADEMARK OFFICE
CERTIFICATE OF CORRECTION

PATENT NO. : 4,152,515
DATED : 5/1/79
INVENTOR(S) : Vincent Lamberti, Mark Konort It is certified that error appears in the above-identified patent and that said Letters Patent are hereby corrected as shown below:

Abstract, line 16: "phosphorous" should read "phosphorus"

Column 2, line 7: "not" should read "now"

Column 5, line 6: The footnote to the paragraph should have an asterisk i.e. Add * before "Sodium linear......"

Column 5, line 3: "alphaolefin" should read "alpha olefin"

Column 5, line 29: "amount" should read "amounts"

Column 5, line 49: Add an asterisk before the footnote to the paragraph "A synthetic....."

Column 6, line 34: "2-3-decyloxypropyl" should read "2-hydroxy-3-decyloxypropyl"

Column 7, line 16: "CA" should read "Ca"

Column 7, line 43: "27" should read "$\underline{27}$"

Column 9, line 63: "27" should read "$\underline{27}$"

UNITED STATES PATENT AND TRADEMARK OFFICE
CERTIFICATE OF CORRECTION

PATENT NO. : 4,152,515

DATED : 5/1/79

INVENTOR(S) : Vincent Lamberti, Mark Konort

It is certified that error appears in the above—identified patent and that said Letters Patent are hereby corrected as shown below:

Column 8, line 10: "348" should read "$\underline{348}$"

Column 8, line 65: "$Ca^{++}1Mg^{++}$" should read "$Ca^{++}/Mg^{++}$"

Column 9, line 4: "$Ca^{++}1Mg^{++}$" should read "$Ca^{++}/Mg^{++}$"

Column 11, line 21: "α-n-dodecyithio" should read "α-n-dodecylthio"

Column 4, line 3: "tetracetate" should read "tetraacetate"

Signed and Sealed this

Twenty-third Day of October 1979

[SEAL]

Attest:

RUTH C. MASON
Attesting Officer

LUTRELLE F. PARKER
Acting Commissioner of Patents and Trademarks